United States Patent [19]

Pohl et al.

[11] 4,026,953

[45] May 31, 1977

[54] SOLVENTS FOR NMR SPECTROSCOPY

[75] Inventors: Ludwig Pohl; Werner Theysohn; Richard Unger, all of Darmstadt, Germany

[73] Assignee: Merck Patent Gesellschaft mit beschrankter Haftung, Darmstadt, Germany

[22] Filed: Oct. 24, 1975

[21] Appl. No.: 625,549

Related U.S. Application Data

[62] Division of Ser. No. 410,280, Oct. 26, 1973, Pat. No. 3,954,410.

[30] Foreign Application Priority Data

Nov. 21, 1972 Germany .......................... 2257005

[52] U.S. Cl. .................... 260/632 R; 260/346.1 R; 260/449.5; 260/459 R; 260/539 A; 260/544 Y; 260/607 D; 260/635 Y; 260/635 M; 260/636; 260/638 A; 260/664; 260/665 G; 260/679 R; 260/681

[51] Int. Cl.² .................. C07C 31/04; C07C 31/08

[58] Field of Search .................... 260/632 R, 642 D

[56] References Cited

UNITED STATES PATENTS

| | | | |
|---|---|---|---|
| 3,702,831 | 11/1972 | Chiarelli et al. ................. | 23/230 R |
| 3,730,687 | 5/1973 | Rondeau .......................... | 23/230 R |
| 3,849,458 | 11/1974 | Dinh-Nguyen et al. ....... | 260/632 R |

OTHER PUBLICATIONS

Nakane et al., "Chem. Abstracts," vol. 59 (1963), col. 1237b.

Dreeskamp et al., "Chem. Abstracts," vol. 55 (1959), col. 12043h.

*Primary Examiner*—Joseph E. Evans
*Attorney, Agent, or Firm*—Millen & White

[57] ABSTRACT

Organic solvents containing less than 0.2 atom percent of $^{13}C$ and which preferably are at least partially deuterated are produced from $^{13}C$-depleted gaseous carbon compounds and are advantageously employed as solvents for $^{13}C$ NMR spectroscopy.

5 Claims, No Drawings

SOLVENTS FOR NMR SPECTROSCOPY

This is a division of application Ser. No. 410,280, filed Oct. 26, 1973, now U.S. Pat. No. 3,954,410.

BACKGROUND OF THE INVENTION

This invention relates to organic solvents with low $^{13}C$ content.

The measurement of absorption spectra of chemical compounds in solution requires solvents having no absorption at all or only a minor absorption in the absorption range of the compound to be investigated.

A large number of solvents are available for infrared, ultraviolet and fluorescent spectroscopy, making it possible to measure spectra of chemical compounds in any desired spectral range. This also holds true for proton NMR spectroscopy, for which proton-free or deuterated solvents are commercially available in a large selection.

For several years, carbon-13 NMR spectroscopy has also been a widely popular auxiliary means for obtaining information on the structure of organic compounds. Informative carbon-13 NMR spectra can be measured of organic compounds whose carbon atom content of carbon having an atomic weight of 13 ($^{13}C$ atoms) is above the natural content of 1.1 atom percent. However, the manufacture of such organic compounds is extremely cumbersome and expensive. Usually, such production is impossible in case of compounds of an unknown structure, for example, natural substances.

The development of the Fourier conversion nuclear resonance technique made it possible also to obtain useful $^{13}C$ NMR spectra of organic compounds having the natural carbon-13 content. In this technique, the quality of the recorded spectrum is dependent on the strongest signal in the spectrum. In the normal case, the compound to be analyzed is utilized, for measuring the spectrum, as a solution in an organic solvent, which almost always is provided in a large excess and thus gives rise to the strongest signal of the spectrum. Therefore, especially in case of test substances which are of moderate or poor solubility, the amount of information extracted from a $^{13}C$ NMR spectrum is adversely influenced to a considerable extent by the solvent. Although this effect can be extensively eliminated, to do so requires very efficient and thus expensive electronic computers.

It is an object of this invention to avoid the disadvantages in carbon-13 NMR spectroscopy caused by the inherent absorption if the solvents.

SUMMARY OF THE INVENTION

In its composition aspect, this invention relates to organic solvents for NMR spectroscopy having a $^{13}C$ content of less than 0.2 atom percent, preferably from 0 to 0.1 atom percent.

In is process aspect, this invention relates to processes for the production of such solvents.

In is method of use aspect, this invention relates to the use of organic solvents having $^{13}C$ content of less than 0.2 atom percent as a solvent for NMR spectroscopy.

DETAILED DISCUSSION

The hydrogen contained in the organic solvents of this invention can be ordinary hydrogen having the atomic weight of 1, or deuterium with the atomic weight of 2. Preferably employed for $^{13}C$ NMR spectroscopy are those solvents of this invention at least a portion of whose hydrogen atoms are deuterium, since such solvents make it possible to measure proton noise decoupled $^{13}C$ spectra without disturbance by the nuclear Overhauser effect.

Preferred organic solvents of this invention having a carbon-13content of less than 0.2 atom percent and which optionally are partially or completely deuterated, are methanol, methylene chloride, chloroform, carbon tetrachloride, acetic acid, ethanol, diethyl ether, nitromethane, acetone, formic acid, dimethyl sulfoxide, dimethylformamide, acetonitrile, tetramethylurea, hexamethylphosphoric triamide, ethylene glycol, ethylene glycol dimethyl ether, dioxane, benzene, tetrahydrofuran, the methyl and ethyl esters of acetic acid, and the methyl and ethyl esters of formic acid.

The organic solvents of this invention having a carbon-13 content of less than 0.2 atom percent, preferably 0 to 0.1 atom percent, are produced in manner known per se in a single- or multistage reaction, preferably from gaseous carbon compounds depleted by conventional isotope separation methods in $^{13}C$ atoms to a content of below 0.2 atom percent, preferably 0 to 0.1 atom percent. An especially preferred starting material is carbon monoxide depleted to a $^{13}C$ content of below 0.2 atom percent, preferably 0 to 0.1 atom percent. Such a carbon monoxide is converted, for example, by treatment with hydrogen or deuterium, into carbon-13-depleted methanol and perdeuterated methanol, respectively, under conditions known from the literature, preferably at a temperature of between 200° and 400° C. and under a pressure of between 3 and 1000 atmospheres gauge, in the presence of a catalyst customary for the methanol synthesis. Especially suitable catalysts are copper oxide and/or zinc oxide based catalysts, preferably activated by a small amount of chromium oxide. In this synthesis, the carbon-13-depleted carbon monoxide and the hydrogen and/or deuterium are utilized preferably in a stoichiometric ratio of 1:2. An excess of hydrogen or deuterium of up to 10% sometimes is advantageous (the ratio values are volume ratios). Advantageously, the synthesis gas is conducted in a cyclic manner over the heated catalyst. The thus-formed $^{13}C$-depleted methanol ($CH_3OH$ and $CD_3OD$, respectively) is condensed in a cooling trap connected after the reactor and an amount of synthesis gas sufficient to maintain the selected pressure is fed, preferably continuously, to the gaseous mixture. The thus-condensed carbon-13-depleted methanol is thereafter purified in a conventional manner, e.g., by fractional distillation.

The thus-obtained pure carbon-13-depleted methanol containing 4 hydrogen atoms or 4 deuterium atoms can be converted into partially deuterated carbon-13-depleted methanol by a conventional isotope exchange process, e.g., by treatment with $D_2O$ or $H_2O$, respectively, in the presence of an alkaline catalyst.

The thus-produced carbon-13-depleted methanol is an excellent solvent for $^{13}C$ NMR spectroscopy. This can be seen by a comparison of the $^{13}C$ NMR spectra of methanol with natural carbon-13 content (1.1 atom percent) and of methanol depleted in $^{13}C$ according to the present invention. The $^{13}C$ NMR spectrum of the predeuterated methanol with natural $^{13}C$ content shows, in the range of between 40 and 55 p.p.m. (chemical shift based on the signal of the tetramethylsilane which represents the zero point of the p.p.m. scale), a septet centered about 47 p.p.m. with a $^{13}C$-$^{2}H$ spin coupling constant of 22 Hz. The $^{13}C$ NMR spectrum of non-deuterated methanol with a natural $^{13}C$ content (1.1 atom percent) shows a quartet about 48 p.p.m. with a $^{13}C$-$^{1}H$ spin coupling constant of 125.7 Hz. In contrast thereto, no absorption signals can be observed in the same frequency ranges in $^{13}C$ NMR spectra, recorded under the same conditions, of non-deuterated or perdeuterated, carbon-13-depleted methanol according to this invention which contains, according to mass-spectroscopic analysis, about 0.06 atom percent of $^{13}C$.

The carbon-13-depleted methanol of this invention is also a valuable intermediate product for the manufacture of a large number of other carbon-13-depleted organic solvents. The latter are produced therefrom in single-stage or multistage reactions, optionally using other intermediate products obtained from carbon-13-depleted carbon monoxide in accordance with standard organic methods, e.g., carbon-13-depleted formamide, carbon-13-depleted carbon dioxide, carbon-13-depleted hydrogen cyanide and carbon-13-depleted formic acid.

The following illustrates the preparation of other carbon-13-depleted organic solvents of this invention employing methanol having a $^{13}C$ content of 0.1 atom percent. It will be obvious to those skilled in the art that any other methanol with a $^{13}C$ content of less than 0.2 atom percent, preferably 0 - 0.1 atom percent, can be employed.

Carbon-13-depleted methanol is converted, for example, by treatment with concentrated hydrochloric acid in the presence of zinc chloride into carbon-13-depleted methyl chloride, by the use of a method known from the literature. From the thus produced methyl chloride, solvents especially important for $^{13}C$ NMR spectroscopy, viz., methylene chloride, chloroform, and carbon tetrachloride, with carbon-13 contents of less than 0.2 atom percent, normally 0 – 0.1 atom percent of $^{13}C$, are obtained by reaction with chlorine, preferably at $-40°$ to $-15°$ C., suitably under irradiation with ultraviolet light. By varying the amount of chlorine employed, the product ratio can readily be controlled. Thus, with a small quantity of chlorine, methylene chloride is predominantly obtained, whereas with an excess of chlorine, carbon tetrachloride is the primary product. The reaction mixtures are separated in a conventional manner by fractional distillation. Depending on the carbon-13-depleted methanol employed as the starting material, normal or deuterated carbon-13-depleted methylene chloride or chloroform is obtained.

By the reaction of carbon-13-depleted methanol with hydrobromic acid or hydriodic acid and/or with bromine or iodine in the presence of phosphorus, carbon-13-depleted methyl bromide or methyl iodide is conventionally obtained. These compounds are especially important intermediates for the preparation of other carbon-13-depleted solvents.

Thus, according to the Hofmann reaction, carbon-13-depleted methylamine, dimethylamine or trimethylamine is produced by the reaction in an aqueous or alcoholic solution of carbon-13-depleted methyl iodide, which will contain hydrogen or deuterium in correspondence with the carbon-13-depleted methanol utilized for the preparation thereof, with ammonia containing hydrogen or deuterium. The quantitative ratio of these amines is controlled by the amount of ammonia utilized. Thus, an excess of ammonia produces primarily carbon-13-depleted methylamine whereas a minimum of ammonia results predominantly in carbon-13-depleted trimethylamine and/or tetramethylammonium iodide. A controlled synthesis of carbon-13-depleted dimethylamine is achieved by conventionally treating an aqueous suspension of calcium cyanamide with carbon-13-depleted dimethyl sulfate.

The carbon-13-depleted dimethylamine is of special significance as an intermediate for the preparation of the valuable carbon-13-depleted solvents dimethylformamide, tetramethylurea, and hexamethylphosphoric triamide.

For the production of carbon-13-depleted dimethylformamide, carbon-13-depleted dimethylamine is reacted at an elevated temperature with formic acid which is depleted in $^{13}C$ in a conventional manner. The carbon-13-depleted formic acid required for this purpose is obtained in a manner known from the literature by reacting an aqueous sodium hydroxide solution (NaOH in $H_2O$ or NaOD in $D_2O$) with carbon-13-depleted carbon monoxide at a pressure of between 10 and 100 atmospheres gauge and a temperature of between 100° and 300° C. and by the subsequent treatment of the thus-obtained carbon-13-depleted sodium formate with sulfuric acid.

Carbon-13-depleted tetramethylurea is produced, for example, by reacting carbon-13-depleted dimethylamine with carbon-13-depleted phosgene in benzene. The carbon-13-depleted phosgene used in this process is obtained, for example, analogously to the process described in U.S. Pat. No. 2,444,289, by reacting carbon-13-depleted carbon monoxide with hydrogen chloride at about 500° C. employing a copper catalyst.

Carbon-13-depleted hexamethylphosphoric triamide can be prepared, for example, by reacting carbon-13-depleted dimethylamine with phosphorus oxychloride analogously to the process described in U.S. Pat. No. 2,752,392. This product, as well as the carbon-13-depleted dimethylformamide and the carbon-13-depleted tetramethylurea, like the starting carbon-13-depleted dimethylamine, contain only up to 0.1 atom percent $^{13}C$ and are valuable solvents for $^{13}C$ NMR spectroscopy, especially for the production of solutions of strongly polar testing substances with higher molecular weights.

Carbon-13-depleted dimethyl sulfoxide having a $^{13}C$ content of 0 – 0.1 atom percent is also useful for the same purpose. This solvent is produced advantageously by reacting a metallic sulfide, preferably an alkali metal sulfide, with carbon-13-depleted methyl iodide in a conventional manner and by subsequent oxidation in accordance with standard methods, e.g., with hydrogen peroxide or by photosensitized reaction with oxygen.

The carbon-13-depleted methyl halides, preferably carbon-13-depleted methyl iodide or methyl bromide, are also valuable intermediates for the preparation of carbon-13-depleted acetic acid and the secondary products thereof. For this purpose, the carbon-13-depleted methyl halide is allowed to react, preferably in the presence of diethyl ether, with magnesium, suitably activated by iodine, to obtain the corresponding methylmagnesium halide, which is thereafter carboxylated with carbon-13-depleted carbon dioxide, which is introduced into the ether solution.

Subsequently, the reaction mixture is decomposed in the usual manner with optionally hydrochloric acid or sulfuric acid. The thus-produced carbon-13-depleted acetic acid is separated and purified, for example by distillation.

The required carbon-13-depleted carbon dioxide can be obtained by combustion of carbon-13-depleted carbon monoxide in an oxygen stream, preferably at a temperature of between 700° and 2000° C. By introducing the combustion gases into an alkali metal hydroxide solution, the corresponding carbon-13-depleted alkali metal carbonates are obtained, from which the carbon-13-depleted carbon dioxide can again be liberated, if necessary, by treatment with an acid.

The acetic acid obtained in the above-described manner has a $^{13}C$ content of 0 – 0.1 atom percent and is suitable as a solvent for $^{13}C$ NMR spectroscopy. This acetic acid is also a valuable intermediate for the preparation of other important solvents, particularly carbon-13-depleted ethanol. The carbon-13-depleted ethanol is especially advantageously prepared from carbon-13-depleted acetic acid by reduction with lithium aluminum hydride or lithium aluminum deuteride in an ether solution. In this process, ethanol is obtained having a carbon-13 content of up to 0.1 atom percent, an important solvent in $^{13}C$ NMR spectroscopy.

Furthermore, the carbon-13-depleted ethanol is used as the starting material for the production of diethyl ether having a carbon-13 content of up to 0.1 atom percent. This solvent is obtained in a conventional manner by the dehydration of carbon-13-depleted ethanol with sulfuric acid at 120°–160° C. or on an aluminum oxide catalyst at 180°–250° C. The thus-obtained carbon-13-depleted diethyl ether is particularly important as a solvent or nonpolar test compounds, the $^{13}C$ NMR spectrum of which is to be measured.

By splitting off water from carbon-13-depleted ethanol with sulfuric acid at 160°–200° C., carbon-13-depleted ethylene is produced which, in turn, is an important starting material for a number of other carbon-13-depleted solvents. Thus, for example, carbon-13-depleted 1,2-dibromoethane is obtained by bromine addition, which is either hydrolyzed to carbon-13-depleted ethylene glycol or is dehydrobrominated to carbon-13-depleted acetylene. The dehydrating dimerization of carbon-13-depleted ethylene glycol in a manner known in the literature produces carbon-13-depleted dioxane, which is an important solvent for $^{13}C$ NMR spectroscopy. Carbon-13-depleted acetylene is trimerized to carbon-13-depleted benzene in the presence of triphenylphosphine nickel carbonyl compounds according to the procedure of Reppe (see Merck Index, Eighth Edition, page 1207) or reacted with carbon-13-depleted formaldehyde (which compound is prepared by standard methods, for example, by dehydrogenation on a silver catalyst at an elevated temperature, from carbon-13-depleted methanol), to obtain carbon-13-depleted, 1,4-butynediol. The carbon-13-depleted butynediol is then hydrogenated to carbon-13-depleted butanediol and the latter is cyclized under dehydration in a conventional manner to carbon-13-depleted tetrahydrofuran.

Carbon-13-depleted methyl ester of formic acid, ethyl ester of formic acid, methyl ester of acetic acid, and ethyl ester of acetic acid are produced from carbon-13-depleted formic acid and acetic acid and carbon-13-depleted methanol and ethanol, respectively, in accordance with standard methods of organic chemistry, e.g., by heating in the presence of a small amount of concentrated sulfuric acid. These esters are well suitable in many cases for use as solvents for $^{13}C$ NMR spectroscopy where conventional solvents cannot be employed.

Carbon-13-depleted acetic acid can be chlorinated with chlorine in a known manner to produce carbon-13-depleted monochloroacetic acid, for example, in the presence of suitably likewise carbon-13-depleted acetyl chloride. From the thus-produced monochloroacetic acid, carbon-13-depleted nitromethane is produced, for example, by reaction, after neutralization wit potassium hydroxide, with sodium nitrite and subsequent decarboxylation. This novel nitromethane is an extremely valuable solvent for $^{13}C$ NMR spectroscopy because many substances, e.g., polycarboxylic acid anhydrides which have too low a solubility in other customary solvents to effect the registration of a sufficiently informative $^{13}C$ NMR spectrum are soluble therein.

By neutralization of carbon-13-depleted acetic acid with lithium hydroxide or lithium carbonate, carbon-13-depleted lithium acetate is obtained from which, by dry distillation in a conventional manner, acetone is produced having a carbon-13 content of between 0 and 0.1 atom percent. This, too, is an especially important solvent for $^{13}C$ NMR spectroscopy.

By the reaction of carbon-13-depleted methanol with chlorosulfonic acid by methods known in the literature, carbon-13-depleted dimethyl sulfate is prepared which likewise is a very valuable reagent for the production of other carbon-13-depleted solvents. Thus, acetonitrile having a carbon-13 content of between 0 and 0.1 atom percent is obtained, for example, by methylating carbon-13-depleted potassium cyanide with carbon-13-depleted dimethyl sulfate. The carbon-13-depleted potassium cyanide can be produced in a manner known in the literature by reacting, at a temperature of between 400° and 700° C., carbon-13-depleted carbon monoxide with ammonia in the presence of a dehydrating catalyst, such as, for example, aluminum oxide and subsequent neutralization of the thus-obtained carbon-13-depleted hydrocyanic acid with potassium hydroxide.

The production of the solvents of this invention having a carbon-13 content of less than 0.2 atom percent, preferably 0 – 0.1 atom percent, is illustrated by the following examples.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

In a circulation system having a capacity of 1.5 liters, in total, and consisting of a heatable reaction tube charge with 400 g. of a mixed catalyst of 55 parts by weight of copper(II) oxide, 30 parts by weight of zinc oxide, and 7 parts by weight of chromium(III) oxide, an associated cooler with condensing trap, and a pump, a synthesis gas mixture is circulated by pumping; this mixture consists of 1 part by volume of carbon monoxide having a carbon-13 content of 0.06 atom % and 2 parts by volume of deuterium. The synthesis gas pressure is 15 atmospheres. The reaction tube is then heated to 240° C. The thus-formed perdeuterated carbon-13-depleted methanol ($CD_3OD$) is collected in the condenser trap, while simultaneously so much new synthesis gas mixture is added that the pressure of 15 atmospheres is maintained. In this apparatus, 70 ml. of tetradeuteromethanol having a carbon-13-content of 0.06 atom % is obtained daily; by a one-time distillation under normal pressure, during which the proportion passing over at 65° C. is collected, a product is obtained which is suitable as a solvent for $^{13}$C NMR spectroscopy.

EXAMPLE 2 a. Under agitation, a solution of 272 g. of anhydrous zinc chloride in 188 g. of concentrated hydrochloric acid is added dropwise to 32 g. of perdeuterated carbon-13-depleted methanol ($CD_3OD$). The mixture is then heated to the boiling point for 2 hours under constant agitation and is then distilled; the reflux condenser, as well as the cooler of the distillation unit are cooled with a cooling medium mixture of about −40° C., and the receiver wherein the distillate is collected is cooled in the same manner. The product is 37.6 g. of deuterated methyl chloride ($CD_3Cl$) having a carbon-13 content of 0.06 atom %; b.p. −24° C. Yield: 79% of theory.

b. Under irradiation with a high-pressure mercury vapor lamp and at −35° to −20° C., 1136 g. of chlorine is introduced into 505 g. of deuterated methyl chloride ($CD_3Cl$) having a carbon-13 content of 0.06 atom % so rapidly that the reaction mixture slightly boils under reflux (dry-ice cooler). Thereafter, the reaction mixture is subjected to fractional distillation. The following distillates are obtained:

76 g. of methyl chloride ($CD_3Cl$; starting material), b.p. −24° C.
127 g. of methylene chloride ($CD_2Cl_2$), b.p. 40° C.
470 g. of chloroform ($CDCl_3$), b.p. 61° C.
25 g. of carbon tetrachloride ($CCl_4$), b.p. 77° C.

The carbon-13 resonance spectra of the thus-produced carbon-13-depleted methylene chloride, chloroform, and carbon tetrachloride are free of absorption signals. In contrast thereto, the carbon-13 nuclear resonance spectrum of deuterated methylene chloride having the natural carbon-13 content shows a quintet about 53.1 p.p.m. with a $^{13}C$-$^2H$ spin coupling constant of 27 Hz. The $^{13}$C NMR spectrum of deuterochloroform with a natural carbon-13 content has a triplet about 77 p.p.m. with a $^{13}C$-$^2H$ spin coupling constant of 31.7 Hz.

EXAMPLE 3 a. 250 ml. of a saturated solution of iodine in perdeuterated carbon-13-depleted methanol is added dropwise to a boiling suspension of respectively 100 g. of red and yellow phosphorus in 750 ml. of perdeuterated carbon-13-depleted methanol. The reaction mixture is further refluxed, and during this step the condensate drips through an iodine-filled vessel having a perforated-screen plate and thus continuously introduces fresh iodine into the reaction mixture. After 2000 g. of iodine in total has thus been added, the reaction mixture is heated under reflux and agitation and is thereafter fractionally distilled. At 40° –41° C., 3370 g. of perdeuterated methyl iodide (94% of theory, based on carbon-13-depleted methanol) is thus distilled off, with a carbon-13-content of about 0.06 atom %.

b. A Daniell's valve extends at one end into a reactor tube of a refractory material; carbon-13-depleted carbon monoxide is conducted through the inner bore of the valve, and oxygen is fed through the outer rim of the valve. The pressure of the gases is adjusted so that carbon monoxide and oxygen exit at a ratio of 2:1. The exiting gaseous mixture is ignited, and the combustion temperature is held at below 2000° C. by cooling the reactor tube. The combustion gases are cooled to room temperature in a cooling pipe following the reactor tube and are introduced into a 50% aqueous potassium hydroxide solution. After the entire amount of potassium hydroxide has been converted into potassium carbonate, the solution is concentrated by evaporation and carbon-13-depleted carbon dioxide is liberated as required from the thus-obtained carbon-13-depleted potassium carbonate by treatment with dilute mineral acids.

c. First of all, 20 ml. of a mixture of 120 g. of carbon-13-depleted methl iodide ($CD_3I$) and 250 ml. of diethyl ether is added to a suspension of 24 g. of magnesium filings in 40 ml. of anhydrous diethyl ether; the reaction mixture is slightly heated after adding an iodine crystal until the Grignard reaction is initiated. Thereafter, the remaining methyl iodide — diethyl ether mixture is added dropwise so quickly that the reaction mixture constantly boils slightly. Then, the mixture is refluxed for one hour. After cooling to room temperature, carbon-13-depleted carbon dioxide is introduced into the reaction mixture under agitation until the temperature of the reaction mixture no longer changes during the continued introduction of the carbon dioxide. Subsequently, 250 ml. of heavy ice water and, dropwise, such an amount of dilute deuterated sulfuric acid are added until the first-formed precipitate is redissolved. The ether phase is separated, and the aqueous phase is extracted three times with respectively 200 ml. of diethyl ether. The combined ether phases are dried over sodium sulfate and distilled. After the diethyl ether has been distilled off, 46.6 g. of acetic acid ($CD_3COOD$) is obtained at a boiling point of 118° C. (88% of theory) with a carbon-13 content of about 0.06 atom %. The product does not produce a signal in the $^{13}$C NMR spectrum, while the spectrum of deuterated acetic acid having the natural carbon-13 content shows a septet about 18.3 p.p.m. ($^{13}C$-$^2H$ coupling constant 19.5 Hz.) and a multiplet about 176.6 p.p.m. ($^{13}C$-$^2H$ coupling constant < 5 Hz.).

EXAMPLE 4 a. 220 g. of extremely pure, dry lithium carbonate is added batchwise under agitation to a solution of 378 g. of carbon-13-depleted acetic acid ($CD_3COOH$) in 500 ml. of water. Then, the mixture is evaporated under reduced pressure. There remains 630 g. of carbon-13-depleted lithium acetate dihydrate, which begins to melt starting with 48° C. and is decomposed at 100° -110° C.

b. 630 g. of carbon-13-depleted lithium acetate dihydrate is melted under agitation and dehydrated by heating for one hour to 130° –200° C. Thereafter, the temperature is gradually elevated and finally maintained at 330° –380° C. for 2.5 hours. The acetone, which is distilled off, is collected in a cooling trap and fractionally distilled for purposes of further purification. At 56° C., 163.5 g. of hexadeuteroacetone (88.5% of theory) is obtained by distillation, with a carbon-13 content of 0.06 atom percent.

The $^{13}$C NMR spectrum of this product does not show any signals, while the spectrum of hexadeuteroacetone having the natural carbon-13 content shows a septet centered about 28 p.p.m. with a $^{13}C$-$^2H$ spin coupling constant of 19.5 Hz. and a hardly dissolved multiplet about 204 p.p.m.

EXAMPLE 5 a. Under agitation, a moderately strong chlorine stream is introduced for 2 hours into a mixture, heated to 100° C., of 200 g. of carbon-13-depleted acetic acid ($CD_3COOD$), 2 g. of iodine, 10 g. of phosphorus pentachloride, and 5 g. of red phosphorus. Then, 50 g. of carbon-13-depleted deuterated acetic acid is furthermore added thereto, and the hot mixture is decanted off from the phosphorus. After cooling to 10° C. for two hours, the thus-crystallized carbon-13-depleted monochloracetic acid is vacuum-filtered, washed with a small amount of carbon-13-depleted acetic acid, and dried, thus obtaining 253 g. of carbon-13-depleted perdeuterated monochloroacetic acid (76.5 % of theory), m.p. 61° C.

b. A solution of 100 g. of carbon-13-depleted monochloroacetic acid ($ClD_2O$-$COOD$) in 100 ml. of heavy water is neutralized with a solution of 56 g. of potassium hydroxide (KOD) in 100 ml. of heavy water. Under agitation, a solution of 300 g. of sodium nitrite in 600 ml. of heavy water is added thereto, and the mixture is gradually heated. During this step, the mixture assumes slowly a brown color and at the same time, carbon-13-depleted carbon dioxide begins to evolve, which is collected by absorption in a potassium hydroxide solution. Once the reaction mixture has assumed a temperature of 105° C., carbon-13-depleted trideuteronitromethane is distilled over with steam. The carbon-13-depleted trideuteronitromethane is separated from the water in the condensate, dried over sodium sulfate, and purified by distillation; b.p. 101°–102° C.; yield; 51 g. (78.5% of theory).

The product does not exhibit any absorption in the $^{13}C$ NMR spectrum, while trideuteronitromethane having the natural carbon-13 content of 1.1 atom % shows a septet about 60.6 p.p.m. with a $^{13}C$-$^2H$ spin coupling constant of 23.7 Hz.

EXAMPLE 6

Under agitation, a solution of 64 g. of perdeuterated carbon-13-depletd acetic acid in 150 ml. of diethyl ether is added dropwise so quickly to a suspension of 25 g. of lithium aluminum deuteride in 50 ml. of diethyl ether that the reaction mixture boils slightly. Thereafter, the reaction mixture is combined with 75 ml. of heavy water, and dilute deuterated sulfuric acid is added thereto until the formed precipitate has been dissolved. The ether phase is separated, and the aqueous phase is extracted three times with respectively 100 ml. of diethyl ether. The combined ether phases are dried over sodium sulfate and subjected to fractional distillation. After the diethyl ether has been distilled off, carbon-13-depleted hexadeuteroethanol passes over at 78°–79° C. Yield: 43 g. (83% of theory).

The $^{13}C$ NMR spectrum of this carbon-13-depleted hexadeuteroethanol with about 0.06 atom % of carbon-13 does not show any absorption bands; in contrast thereto, a hexadeuteroethanol havng the natural carbon-13 content shows a septet about 15.8 p.p.m. ($^{13}C$-$^2H$ spin coupling constant 19.5 Hz.) and a quintet about 55.4 p.p.m. ($^{13}C$-$^2H$ spin coupling constant 22.0 Hz.).

EXAMPLE 7

520 g. of carbon-13-depleted hexadeuteroethanol is distilled from a distillation flask via a heatable column at a rate of 15–20 drops of ethanol per minute through a reaction tube heated to 200° C., this tube being filled with a dehydration catalyst; the catalyst consists of aluminum alum which is finely distributed over kieselguhr. The outlet of the reaction tube leads into a receiver, cooled to −60° C., wherein unreacted ethanol, water, and carbon-13-depleted decadeuterodiethyl ether are condensed. After separation of the aqueous ethanol, which still contains 96 g. of carbon-13-depleted hexadeuteroethanol, the thus-obtained decadeuterodiethyl ether with a carbon-13 content of about 0.06 atom % is distilled; b.p. 34°–35° C. Yield; 236 g. (69% of theory).

EXAMPLE 8 a. In an agitator-equipped autoclave, carbon-13-depleted carbon monoxide is added under a pressure of up to 40 atmospheres to a solution of 410 g. of sodium deuteroxide in 2 l. of heavy water. The mixture is then heated under agitation to 195° C., during which step the pressure rises at first to 60 atmospheres, but thereafter drops again and is maintained at about 50 atmospheres by adding additional carbon-13-depleted carbon monoxide under pressure at half-hour intervals. After about 20 hours, no additional carbon monoxide is absorbed any more. After the apparatus has been cooled, the excess carbon-13-depleted carbon monoxide is exhausted (and collected for further use), and the thus-obtained solution of deuterated carbon-13-depleted sodium formate is evaporated; yield: 660 g. (95.7% of theory).

b. 345 g. of anhydrous carbon-13-depleted sodium formate (DCOONa) is introduced in incremental portions under agitation and cooling to 5°–10° C. into 260 g. of concentrated deuterated sulfuric acid. Then, the reaction mixture is gradually heated to 60° C. and the thus-liberated carbon-13-depleted deuterated formic acid is distilled off therefrom under reduced pressure. Yield: 195 g. (83.3% of theory).

EXAMPLE 9 a. Under agitation and cooling, at a temperature of −10° C., 72 g. of carbon-13-depleted methanol ($CD_3OD$) is added dropwise during the course of about 90 minutes to 250 g. of chlorosulfonic acid so that the temperature does not exceed −5° C. Then, the reaction mixture is heated to 140° C. under a pressure of 15 mm. Hg, during which step carbon-13-depleted perdeuterated dimethyl sulfate is distilled off. Yield: 95 g. (71.8% of theory).

b. Under agitation, 74 g. of perdeuterated carbon-13-depleted dimethyl sulfate is added dropwise to a suspension of 88 g. of ground calcium cyanamide (55% purity) in 100 ml. of water. Thereafter, the mixture is refluxed for 30 minutes and, after cooling, combined with 100 g. of sodium hydroxide. Then, the thus-formed carbon-13-depleted hexadeuterodimethylamine is distilled off with steam and collected in a receiver charged with 300 ml. of 20% hydrochloric acid. Subsequently, the content of the receiver is evaporated and the residue extracted with hot chloroform in a Soxhlet apparatus. After evaporation of the chloroform extracts, there remains 39 g. of carbon-13-depleted hexadeuterodimethylamine hydrochloride (80% of theory), m.p. 170° C.

c. A mixture of carbon-13-depleted hexadeuterodimethylamine (produced by dropping a concentrated aqueous solution of dimethylamine hydrochloride on an excess of potassium carbonate heated to 80° C.) and air in a volume ratio of about 1:1 is passed under suction pressure through 94 g. of partially deuterated carbon-13-depleted formic acid (DCOOH) at 95° C. for 8 hours. Then, the thus-formed crude heptadeuterodimethylformamide with a carbon-13 content of about 0.06 atom % is distilled; b.p. 153° C. Yield: 117 g. (73% of theory).

The product shows no absorption whatever in the $^{13}$C NMR spectrum. In contrast thereto, heptadeuterodimethylformamide having the natural carbon-13 content has two septets about 29 and 34.1 p.p.m. ($^{13}$C-$^2$H spin coupling constant 22 Hz.) and a triplet at 161.6 p.p.m. ($^{13}$C-$^2$H spin coupling constant 29.3 Hz.).

The following product is produced analogously:

Nonadeuterodimethylacetamide, having a carbon-13 content of about 0.06 atom %, b.p. 165° C. Yield: 84% of theory.

EXAMPLE 10

At room temperature, 99 g. of carbon-13-depleted phosgene (by introducing carbon tetrachloride dropwise into fuming sulfuric acid with 45% of sulfur trioxide at 78° C.) is introduced into a solution of 204 g. of carbon-13depleted hexadeuterodimethylamine in 400 ml. of anhydrous benzene. Thereafter, the reaction mixture is heated for two hours to the boiling point. After cooling, the thus-crystallized carbon-13-depleted hexadeuterodimethylamine hydrochloride is filtered off, and the benzene is distilled off. The remaining dodecadeuterotetramethylurea having a carbon-13 content of about 0.06 atom % is distilled under reduced pressure; b.p.$_{18}$ 91° C. Yield: 93.5 g. (73% of theory).

EXAMPLE 11

Under agitation, a solution of 62 g. of phosphorus oxychloride in 65 ml. of di-n-butyl ether is added during one hour to a solution of 218 g. of carbon-13-depleted hexadeuterodimethylamine in 450 ml. of di-n-butyl ether. Then, the reaction mixture is heated in an autoclave for 2 hours to 95° C. After the excess dimethylamine has been exhausted and the mixture has been cooled to room temperature, the mixture is filtered off from the crystallized dimethylamine hydrochloride. After the solvent has been distilled off, the remaining octadecadeuterohexamethylphosphoric triamide with a carbon-13-content of about 0.06 atom % is distilled under reduced pressure; b.p.$_{.3}$ 80° C. Yield: 65.7 g. (82.5% of theory).

EXAMPLE 12 a. An internally glazed porcelain tube having a length of 70 cm. and an internal diameter of 7 cm. is filled with 1000 g. of granular aluminum oxide and heated to 570° C. by means of an electric heating mantle. A gaseous mixture preheated to 300° –400° C. of 1 part by volume of ammonia and 4 parts by volume of carbon-13-depleted carbon monoxide is passed through this tube at a rate of 1500 l. per hour. The gases exiting from the reaction tube are first cooled with water, and then the thus-produced hydrogen cyanide is condensed therefrom in a receiver cooled to −20° C. with methanol/dry ice. The yield in carbon-13-depleted, liquid hydrogen cyanide is 100 g. per hour.

b. A solution of 112 g. of potassium hydroxide in 350 ml. of water is added under cooling to a solution of 54 g. of hydrogen cyanide in 180 ml. of water so that the temperature does not rise above 40° C. Subsequently, the reaction mixture is evaporated under reduced pressure, yielding 130 g. of carbon-13-depleted potassium cyanide.

c. Under agitation and cooling to 10° C., 125 g. of carbon-13-depleted hexadeuterodimethyl sulfate is added dropwise durng the course of one hour to a solution of 130 g. of carbon-13-depleted potassium cyanide in 60 ml. of water. Then, the mixture is agitated for one hour at room temperature and distilled. At 76° –82° C., crude carbon-13-depleted trideuteroacetonitrile is distilled off, which is purified by a further distillation; b.p. 81° –82° C. Yield: 76 g. (92.5% of theory).

The $^{13}$C NMR spectrum of the product does not show an absorption signal. In contrast thereto, the spectrum of trideuteroacetonitrile having the natural carbon-13 content has a septet about 0.2 p.p.m. ($^{13}$C-$^2$H spin coupling constant 22 Hz.) and a weakly resolved multiplet about 116.9 p.p.m.

EXAMPLE 13 a. During the course of 2 hours and under vigorous agitation, 580 g. of carbon-13-depleted trideuteromethyl iodide is added dropwise to a solution of 720 g. of sodium sulfide nonahydrate in 50 ml. of water. Thereafter, the reaction mixture is heated to the boiling point for three hours under stirring, and the thus-formed carbon-13-depleted hexadeuterodimethyl sulfide is then distilled off; b.p. 37°–38° C. Yield: 107 g. (78.5% of theory).

b. Under agitation and cooling to 10° C., 460 g. of 30% deuterium peroxide (D$_2$O$_2$) is added dropwise to a solution of 340 g. of carbon-13-depleted hexadeuterodimethyl sulfide in 2 l. of acetone. Then, the mixture is stirred for another 2 hours at 10° C. and thereafter allowed to stand at room temperature for 4 days. Then, 300 g. of solid iron(II) sulfate is added thereto and the mixture agitated for 2 hours at room temperature. Subsequently, 250 g. of anhydrous sodium sulfate is added; after another hour of agitation, the reaction mixture is filtered and the solvent evaporated. The residue, consisting of hexadeuterodimethyl sulfoxide with a carbon-13 content of about 0.06 atom %, is then distilled under reduced pressure. Boiling point$_{17}$ 83° C. Yield: 308 g. (73.3% of theory).

The $^{13}$C NMR spectrum of this product does not show an absorption signal, while the spectrum of hexadeuterodimethyl sulfoxide having the natural content of carbon-13 has a septet about 39.6 p.p.m. with a $^{13}$C-$^2$H spin coupling constant of 22 Hz.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An at least partially deuterated methanol or ethanol having a carbon-13 content of not more than 0.2 atom percent.

2. A perdeuterated methanol according to claim 1.

3. A perdeuterated ethanol according to claim 1.

4. A perdeuterated methanol according to claim 1 having a carbon-13 content of not more than 0.1 atom percent.

5. A perdeuterated ethanol according to claim 1 having a carbon-13 content of not more than 0.1 atom percent.

* * * * *